(12) United States Patent
Suarez

(10) Patent No.: US 8,876,697 B2
(45) Date of Patent: Nov. 4, 2014

(54) DEVICE FOR MAINTAINING AN ERECTION

(76) Inventor: Fernando Suarez, Costa Mesa, CA (US)

( * ) Notice: Subject to any disclaimer, the term of this patent is extended or adjusted under 35 U.S.C. 154(b) by 353 days.

(21) Appl. No.: 13/415,665

(22) Filed: Mar. 8, 2012

(65) Prior Publication Data

US 2013/0237752 A1 Sep. 12, 2013

(51) Int. Cl.
*A61F 5/41* (2006.01)

(52) U.S. Cl.
USPC .......................................................... 600/41

(58) Field of Classification Search
CPC ....... A61H 19/44; A61H 19/32; A61H 19/00; A61H 19/30; A61H 19/50; A61H 19/40; A61F 6/04; A61F 5/41; A61F 2005/411; A61F 2005/414; A61F 2005/415; A61F 2005/417
USPC ................................ 600/38, 39, 41; 128/844
See application file for complete search history.

(56) References Cited

U.S. PATENT DOCUMENTS

| 4,523,584 | A | * | 6/1985 | Yachia et al. ................... 600/38 |
| 4,960,113 | A | | 10/1990 | Seeberg-Elverfeldt |
| 5,445,594 | A | | 8/1995 | Elist |
| 5,509,891 | A | | 4/1996 | DeRidder |
| 5,522,787 | A | | 6/1996 | Evans |
| 5,623,945 | A | | 4/1997 | Shecterle |
| 5,823,939 | A | | 10/1998 | Tsagarakis |
| 6,193,753 | B1 | | 2/2001 | Nordheim et al. |
| 2007/0186935 | A1 | * | 8/2007 | Wang et al. ................... 128/844 |

* cited by examiner

Primary Examiner — Christine Matthews
(74) Attorney, Agent, or Firm — Vladi Khiterer

(57) ABSTRACT

A device for maintaining an erection has tubes connected to C-shaped balloons disposed at the base and neck of the penis. The air pressure inside the tubes helps to maintain the erection, while the C-shaped balloons help to retain the blood inside Corpora Cavernosa due to the choke-like grip around the base and neck of the penis. The air pressure is supplied by a pump actuated by movements of a pubic bone during sexual activity.

1 Claim, 4 Drawing Sheets

DEVICE FOR MAINTAINING AN ERECTION

BACKGROUND OF THE INVENTION

This invention relates to a removable (i.e. non-implantable) device for maintaining an erection.

Non-implantable devices for achieving and/or maintaining an erection of the prior art require external sources of air or liquid pressure, such as pumps, to operate. They are difficult to maintain in a hygienic condition and also interfere with the stimulation of the penis. What is needed is a removable and reusable device that does not require an external pump, easy to maintain in a hygienic condition and does not interfere with the stimulation of the penis.

SUMMARY OF THE INVENTION

The device for maintaining an erection according to this invention satisfies this need. It has tubes disposed substantially parallel to a penis connected to C-shaped balloons disposed at the base and neck of the penis. A pump is actuated by movements of a pubic bone during sexual activity. As the air pressure inside the tubes increases, they become rigid, helping to maintain the erection, while the C-shaped balloons help to retain the blood inside Corpora Cavernosa due to the choke-like grip around the base and neck of the penis. Accordingly, the device according to this invention prolongs the duration of the natural erection.

DESCRIPTION OF THE INVENTION

The preferred embodiment of this invention will be better understood in reference to FIG. 1 through FIG. 4. The same numerals refer to the same elements in all figures.

Figure 1:
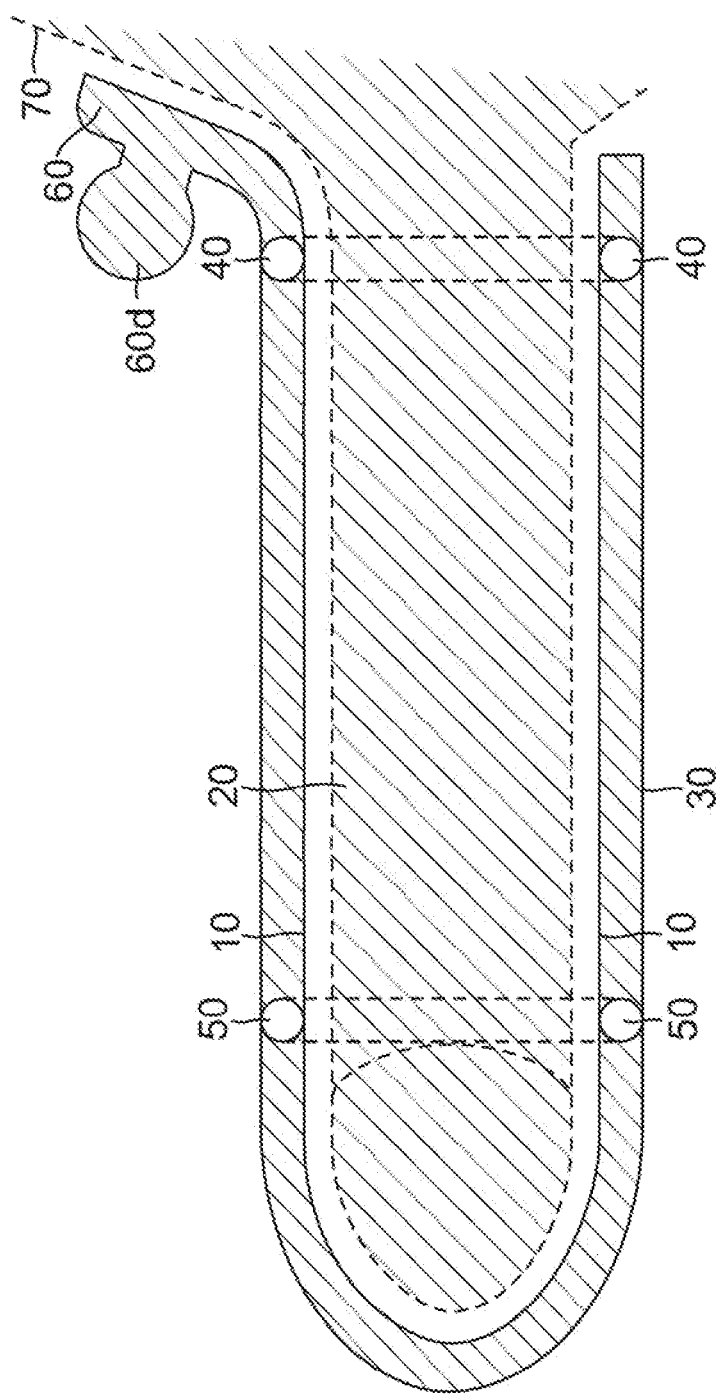
FIG. 1 is a cross sectional view of the device for maintaining an erection according to this invention.

Viewing now FIG. 1, it shows a cross-sectional view of the device for maintaining an erection according to this invention. Numeral 10 indicates a first layer. First layer 10 receives and snuggly retains a penis of a user indicated by numeral 20. Numeral 30 indicates a second layer. Second layer 30 is disposed adjacent to first layer 10.

In the preferred embodiment described in reference to FIG. 1 through 4, first layer 10 is made of silicone having a first durometer and second layer 30 is made of silicone having a second durometer. It is preferable that second layer 30 is softer than first layer 10, thus the first durometer is higher than the second durometer. In the preferred embodiment, the first durometer is 40 and the second durometer is 20. Further, in the preferred embodiment, first layer 10 and second layer 30 form a condom-like shape, being enclosed at the tip of penis 20. In other embodiments, area near the tip of penis 20 may be open.

In the preferred embodiment, first layer 10 and second layer 30 are made from the Medical Class VI Liquid Silicone, which allows the device to withstand temperatures from −50 F to +400 F. This material makes the device 100% hypoallergenic and permits using a dishwasher, an autoclave or boiling water to wash and disinfect.

Figure 2:
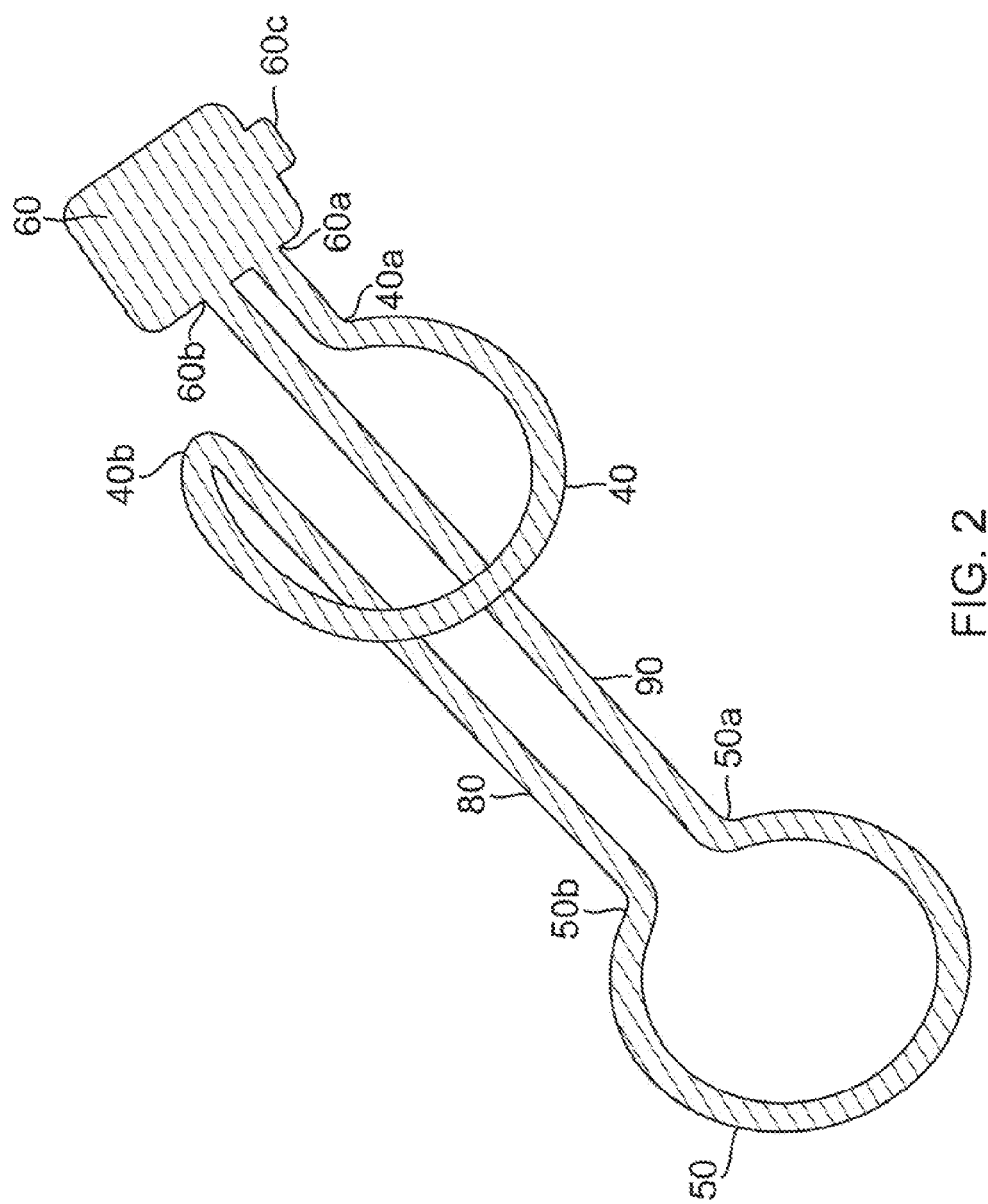
FIG. 2 is a perspective view of the device for maintaining an erection according to this invention showing a first and second C-shaped balloons, a first and second tube and a pump.

Viewing now, simultaneously, FIG. 1 and FIG. 2 (FIG. 2 does not show first layer 10 and second layer 20), numeral 40 indicates a first C-shaped balloon. First C-shaped balloon 40 is disposed adjacent to the base of penis 20, in a plane substantially perpendicular to the longitudinal axis of penis 20. First C-shaped balloon 40 comprises open proximal and distal ends indicated by numerals 40a and 40b, respectively.

Numeral 50 indicates a second C-shaped balloon. Second C-shaped balloon 50 is disposed adjacent to the neck of penis 20, in a plane substantially perpendicular to the longitudinal axis of penis 20. Second C-shaped balloon 50 comprises open first and second ends indicated by numerals 50a and 50b, respectively.

Numeral 60 indicates a pump. Pump 60 comprises an inlet indicated by numeral 60a, an outlet indicated by numeral 60b, a release valve indicated by numeral 60c and a squeeze bulb indicated by numeral 60d. Inlet 60a comprises a one way inlet valve. Outlet 60b comprises a one way outlet valve. Squeeze bulb 60d is disposed adjacent to a pubic bone of the user indicated by numeral 70. In the preferred embodiment, squeeze bulb 60d delivers 1 cc of air per squeeze.

Numeral 80 indicates a first tube. First tube 80 is disposed substantially parallel to the longitudinal axis of penis 20. First tube 80 begins at distal end 40b and terminates at second end 50b. First tube 80 places distal end 40b and second end 50b in pneumatic communication.

Numeral 90 indicates a second tube. Second tube 90 is disposed substantially parallel to the longitudinal axis of penis 20. Second tube 90 begins at outlet 60b and terminates at first end 50a. Second tube 90 places outlet 60b and first end 50a in pneumatic communication.

Proximal end 40a is in pneumatic communication with inlet 60a. Accordingly, first C-shaped balloon 40, second C-shaped balloon 50, first tube 80, second tube 90 and pump 60 are in pneumatic communication and maintain the same air pressure therein. Release valve 60c opens when air pressure inside first C-shaped balloon 40, second C-shaped balloon 50, first tube 80 and second tube 90 exceeds a predetermined value. In the preferred embodiment, release valve 60c opens when the amount of air inside first C-shaped balloon 40 and second C-shaped balloon 50 exceeds 30 cc.

First C-shaped balloon 40, second C-shaped balloon 50, first tube 80 and second tube 90 are embedded between first layer 10 and second layer 30.

In the preferred embodiment described in reference to FIG. 1 through 4, first C-shaped balloon 40 and the second C-shaped balloon 50 are made from silicone having a third durometer. First tube 80 and second tube 90 are made from silicone having a fourth durometer. In other embodiments, first tube 80 and second tube 90 can be made from other materials, such as thermoplastic elastomers known as the TPEs, or other plastic materials.

It is desirable that first C-shaped balloon 40 and the second C-shaped balloon 50 be relatively soft and easy to inflate. Therefore, the fourth durameter is higher than the first durometer and the second durometer is higher than the third durometer. In the preferred embodiment, the third durometer is 10 and the fourth durometer is 80.

Figure 3:
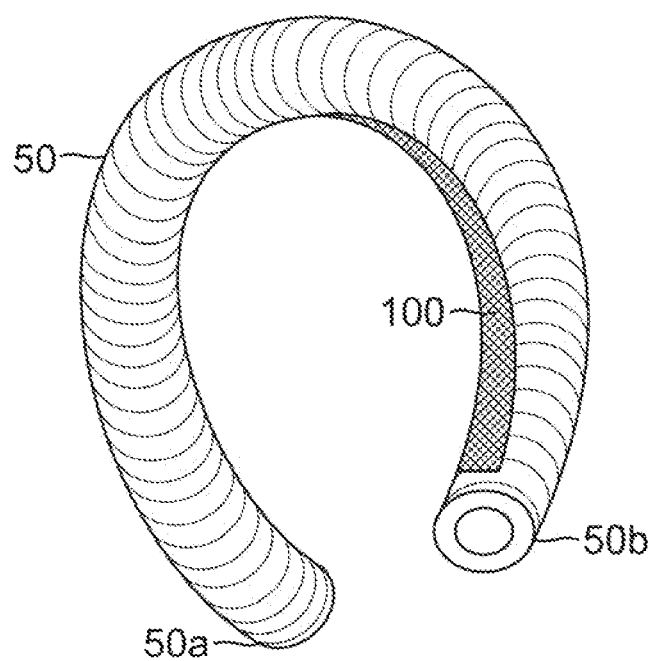
FIG. 3 shows a C-shaped balloon and restriction means in a deflated condition.
Figure 4:
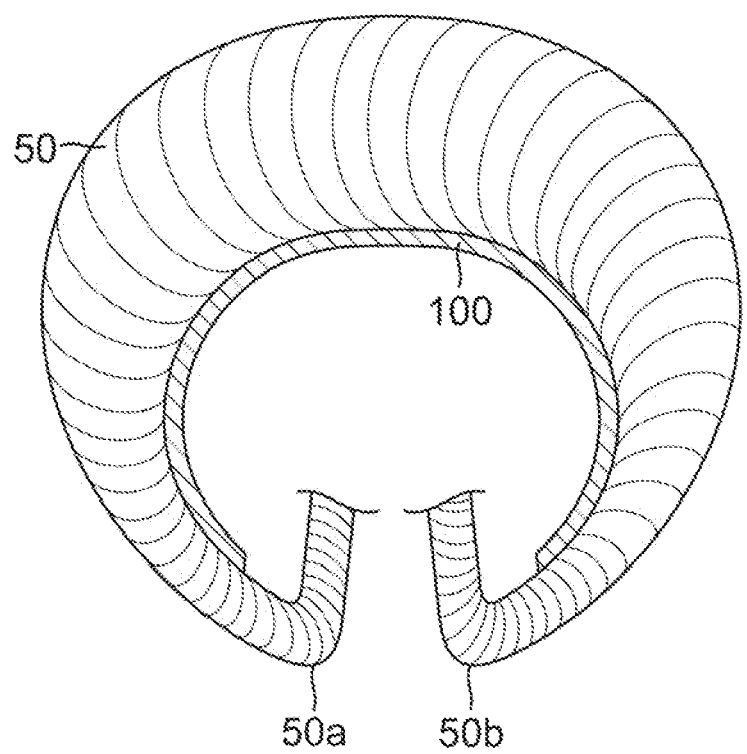
FIG. 4 shows a C-shaped balloon and restriction means in an inflated condition.

Viewing now, simultaneously, FIG. 3 and FIG. 4, first C-shaped balloon 40 and second C-shaped balloon 50 comprise a restriction means indicated by numeral 100 (only second C-shaped balloon 50 is shown in FIG. 3 and FIG. 4, however, restriction means 100 is identical in both first C-shaped balloon 40 and second C-shaped balloon 50). Due to restriction means 100, inflation causes first C-shaped balloon 40 and second C-shaped balloon 50 to curve inward in a choke-like manner around penis 20, as shown in particular in FIG. 4. In the preferred embodiment shown in FIG. 1 through FIG. 4, restriction means 100 is a non-stretchable tape fixedly attached to first C-shaped balloon 40 and second C-shaped balloon 50 adjacent to first layer 10, preferably 1/16" wide.

The device for maintaining an erection according to this invention goes over penis 20 while it is in full or partial erection. A small amount of pressure can be applied manually in order to keep the device in place at the beginning by depressing squeeze bulb 60d. After the device is in place, squeeze bulb 60d is actuated by movements of pubic bone 70 during sexual activity. Specifically, due to its location adjacent to pubic bone 70, squeeze bulb 60d abuts a sexual partner. Back and forth movements of pubic bone 70 cause it to be squeezed and thus gently increase the air pressure inside first C-shaped balloon 40, second C-shaped balloon 50, first tube 80 and second tube 90. This causes first C-shaped balloon 40 and second C-shaped balloon 50 to inflate, thereby curving inside and tightening around the neck and base of penis 20.

Erection is maintained by two Corpora Cavernosa vessels filling up with blood. As blood pressure inside Corpora Cavernosa decreases, so is the degree of the erection. That is when the air pressure inside first tube 80 and second tube 90 increases, helping to maintain the erection, while first C-shaped balloon 40 and second C-shaped balloon 50 help to retain the blood inside Corpora Cavernosa due to the choke-like grip around the base and neck of penis 20. Accordingly, the device according to this invention prolongs the duration of the natural erection. The device can be removed even when fully pressurized. Alternatively, release valve 60c can be used to assist with removal. While the present invention has been described and defined by reference to the preferred embodiment of the invention, such reference does not imply a limitation on the invention, and no such limitation is to be inferred. The invention is capable of considerable modification, alteration, and equivalents in form and function, as will occur to those ordinarily skilled and knowledgeable in the pertinent arts, including a free standing electrical appliance incorporating this invention. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

I claim:
1. A device for maintaining an erection comprising:
a first layer configured to be receiving and snuggly retaining a penis of a user therein;
a second layer disposed adjacent to the first layer;
a first C-shaped balloon configured to be disposed adjacent to a base of the penis, in a plane substantially perpendicular to a longitudinal axis of the penis, the first C-shaped balloon comprising an open proximal end and an open distal end;
a second C-shaped balloon configured to be disposed adjacent to a neck of the penis, in a plane substantially perpendicular to the longitudinal axis of the penis, the second C-shaped balloon comprising an open first end and an open second end;
a pump comprising a squeeze bulb configured to be disposed adjacent to a pubic bone of the user, an inlet comprising a one way inlet valve, an outlet comprising a one way outlet valve and a release valve;
a first tube configured to be disposed substantially parallel to the longitudinal axis of the penis, the first tube beginning at the open distal end and terminating at the open second end, placing the open distal end and the open second end in pneumatic communication;
a second tube configured to be disposed substantially parallel to the longitudinal axis of the penis, the second tube beginning at the outlet and terminating at the open first end, placing the outlet and the open first end in pneumatic communication;
wherein the first C-shaped balloon, the second C-shaped balloon, the first tube and the second tube are embedded between the first layer and the second layer;
wherein the squeeze bulb is configured to be actuated by movements of the pubic bone during sexual activity;
wherein the open proximal end is in pneumatic communication with the inlet;
wherein the first and second C-shaped balloons comprise restriction means, such that inflation causes the first and second C-shaped balloons to curve inward in a choke-like manner around the penis;
wherein the release valve opens when air pressure inside the first C-shaped balloon, second C-shaped balloon, the first tube and the second tube exceeds a predetermined value;
wherein the first layer is made from silicone having a first durometer, the second layer is made from silicone having a second durometer, the first durometer being higher that the second durometer;
wherein the first C-shaped balloon and the second C-shaped balloon are made from silicone having a third durometer;
wherein the first tube and the second tube are made from silicone having a fourth durometer;
wherein the fourth durometer is higher than the first durometer and the second durometer is higher than the third durometer;
wherein the restriction means comprises a non-stretchable tape fixedly attached to the first and second C-shaped balloons adjacent to the first layer.

* * * * *